US005955649A

United States Patent [19]

Hirota et al.

[11] Patent Number: 5,955,649

[45] Date of Patent: Sep. 21, 1999

[54] GENE EXPRESSION REGULATORY DNA, EXPRESSION CASSETTE, EXPRESSION VECTOR AND TRANSGENIC PLANT

[75] Inventors: Naohiko Hirota; Makoto Kihara; Hisao Kuroda; Kazutoshi Ito, all of Gunma-ken, Japan

[73] Assignee: Sapporo Breweries Ltd., Tokyo, Japan

[21] Appl. No.: 08/899,336

[22] Filed: Jul. 23, 1997

[30] Foreign Application Priority Data

Jul. 23, 1996 [JP] Japan .................................... 8-193433

[51] Int. Cl.[6] ............................ C12N 15/82; C12N 5/04; A01H 4/00

[52] U.S. Cl. ........................ 800/278; 536/23.6; 536/24.1; 435/320.1; 435/410

[58] Field of Search ................................. 536/23.6, 24.1; 435/320–321, 410; 800/205, DIG. 55

[56] References Cited

FOREIGN PATENT DOCUMENTS 0 571 741 A2 12/1993 European Pat. Off. .

OTHER PUBLICATIONS

Sorenson M. et al, "Hordein promoter methylation and transcriptional activity in wild–type and mutant barley endosperm", Molecular and General Genetics, vol. 250, No. 6, Apr. 10, 1996, pp. 750–760.

Cho M. et al, "Expression of hordein promoter–uidA fusions in transgenic barley plants; endosperm–specific B–and D–hordein promoter gene expression in transgenic plant, for potential crop improvement", In Vitro, vol. 32, No. 3, 1996, pp. 103a XP002054427, see abstract.

Thomas M. and Flavell R., "Identification of an ebhancer element for the endosperm–specific expression of high molecular weight glutenin", The Plant Cell, vol. 2, No. 11, Dec. 1990, pp. 1171–1180.

Matzke and Matzke Plant Physiol. 1995. vol. 107: 679–685.

Peltonen et al. Hereditas. 1994. vol. 120:231–239.

Sorenson et al. Mol Gen Genet. 1996 vol. 250:750–760.

Finnegan and McElroy. Bio/Technology. 1994. vol. 12:833–888.

Wan and Lemaux. Plant Physiol. 1994. vol. 104:37–48.

*Primary Examiner*—Gary Benzion
*Assistant Examiner*—Ousama Zaghmout
*Attorney, Agent, or Firm*—Oblon, Spivak, McClelland, Maier & Neustadt, P.C.

[57] ABSTRACT

The present invention provides new gene expression regulatory DNA. This gene expression regulatory DNA comprises a promotor region derived from the barley D-hordein gene enabling the expression of a desired gene, and a regulatory region for regulating the expression of said gene based on said promoter region. This regulatory region consists at least of an activating region to activate the expression of said gene and a suppressing region to suppress the same.

Use of this gene expression regulatory DNA enables controlling as desired the expression of gene within a plant cell such as barley.

17 Claims, No Drawings

```
                         SEQUENCE LISTING


(1) GENERAL INFORMATION:

   (iii) NUMBER OF SEQUENCES: 8


(2) INFORMATION FOR SEQ ID NO:1:

     (i) SEQUENCE CHARACTERISTICS:
          (A) LENGTH: 1739 base pairs
          (B) TYPE: nucleic acid
          (C) STRANDEDNESS: double
          (D) TOPOLOGY: linear

    (ii) MOLECULE TYPE: DNA (genomic)

    (xi) SEQUENCE DESCRIPTION: SEQ ID NO:1:

CTGCAGATTT GCAAAAGCAA TGACTAACAG ATACATATAT TGCAAAAAAA ACAGAGGATA     60

ATCACTTTTA TTAGATGAAA TAAACAGATC AATTTACATA AGTCCTCACT TCTCCAAACA    120

GTATTCAGGA CCATGATAAA ACCGATTACG TAGCTCTGTT TTGGAAGATC CAAATCCTCA    180

AGTTGAGTTT CATTAATTGG AATCGATTGT ATGCTAAACA CGATGAACAA ATGGTGGGTT    240

ACGTGGCATA GCATACAACT ATTCCCCTAT TATTCTGCAT GCATGATCTC AATCGGACTC    300

CTTCCTAGTT CCTAGTTGGC TCTGCTTTGA ACTTTCATCC ACATCTCTTT GAGTTATTAT    360

TAACAGACGC AAGAAACATT TTTTTGCGCT AAGCCAAGGT GAGGCAAGGT CGCATTGGAG    420

GACTGATGGA CTGGCTTCGA TGGATTATGA TATACTCGGT TTTGCCTGTT TGACTGTTAC    480

GTTTTTCTAA TTTTGTGGTT AGGAATTTTT CGCCGCAGAG TATAGAATAA CTAAGCTCAA    540

CACAAACAAT TTAGCAAGCA CATTAAACTG GGATCGTAGG AGCGCACCTG GATTTTGTTG    600
```

```
GTTGATGGTG GATGAAATGG GTGAATTTAA TAACTGATAT AGTGTCAGTG CAACGGAAGC    660
CCATTTTTCA TACAAGTTAT TAATATTGTC AACATTTGTC AACAAACAAA TGTTTAACTC    720
AGGTTTGCAA TTATGAAGCC CCAATTATAA GAAGGGGATA TTATGATGGC GTGAGCAAGT    780
GATAAGGCCA AGGGGAGAAG AAGTGCAGCA TCTACGCAGC CCAGTGAAAG ATAGTGAAAA    840
TACAGAGAGG CAGGGACGGG GGAGCAACAC ATGGAAATCA TAGAAGAACA AAAGAGTTTA    900
AACATAGGAG GCAGATATAA TGGACAGCTA AATCTGCATT ATCTCATTTG GGAAATGAAA    960
AAAATAATCC TATTCTTGTG TAAATCAAAA CTATTTGCCG CGAATTTTCT TCGAAGATCC   1020
TGTGTTAATT TTAGACACGG CTGACCAAAG GTTTTCAATT AGTTGAGTTT TGTCACGGAA   1080
AGGTGTTTCC ATACATCCAA AAATTCTAAA AACTTTTTGA TACGGCGCGT TCGTAGCATA   1140
GCTAGATGTT GTGAGTCACT GGATAGATAT TGTGAGTCAT ATCGTGGATT TGTGTTGCCT   1200
GCAAATCCAA CTACATGACA AGCAACAAAT GAGCTTTTGG AAAGATGATT TCTCAATTTA   1260
CCAGTTCCAT GCAAGCTACC TTCCACTACT CGACATGCTT AAAAGCTTCG AGTGCCCGCC   1320
GATTTGCCAG CAATGGCTAA CAGACACATA TTCTGCCAAA ACCCCAGAAC AATAATCACT   1380
TCTCGTAGAT GAAGAGAACA GACCAAGATA CAAACGTCCA CGCTTCAGCA AACAGTACCC   1440
CAGAACTAGG ATTAAGCCGA TTACGCGGCT TTAGCAGACC GTCCAAAAAA ACTGTTTTGC   1500
AAAGCTCCAA TTCCTCCTTG CTTATCCAAT TTCTTTTGTG TTGGCAAACT GCACTTGTCC   1560
AACCGATTTT GTTCTTCCCG TGTTTCTTCT TAGGCTAACT AACACAGCCG TGCACATAGC   1620
CATGGTCCGG AATCTTCACC TCGTCCCTAT AAAAGCCCAG CCAATCTCCA CAATCTCATC   1680
ATCACCGAGA ACACCGAGAA CCACAAAACT AGAGATCAAT TCATTGACAG TCCACCGAG    1739
```

(2) INFORMATION FOR SEQ ID NO:2:

(i) SEQUENCE CHARACTERISTICS:
(A) LENGTH: 2296 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:2:

```
CAAAACTAGA GATCAATTCA TTGACAGTCC ACCGAGATGG CTAAGCGGCT GGTCCTCTTT     60
GTGGCGGTAA TCGTCGCCCT CGTGGCTCTC ACCACCGCTG AACGTGAGAT CAATGGGAAC    120
AACATTTTCC TTGATAGCCG CTCTAGGCAG CTACAGTGTG AGCGCGAGCT CCAGGAGAGC    180
TCGCTCGAGG CGTGCCGGCG GGTCGTGGAC CAACAGCTGG TTGGCCAGCT GCCATGGAGC    240
ACGGGGCTCC AGATGCAGTG CTGCCAGCAG CTTCGGGACG TCAGCCCCGA GTGCCGCCCC    300
GTCGCCCTCA GCCAGGTCGT GAGGCAATAC GAGCAGCAAA CCGAGGTGCC ATCCAAGGGA    360
GGATCCTTCT ACCCGGGCGG GACCGCACCG CCGCTGCAGC AAGGAGGATG GTGGGGAACC    420
TCTGTAAAAT GGTACTACCC AGACCAAACT TCTTCGCAAC AGTCATGGCA AGGGCAACAA    480
GGGTACCACC AAAGCGTAAC TTCTTCCCAG CAGCCAGGAC AAGGGCAGCA AGGGTCCTAC    540
CCAGGTTCAA CTTTCCCGCA GCAGCCAGGA CAAGGACAAC AACCAGGACA GAGGCAGCCA    600
TGGTCCTATC CAAGTGCAAC TTTCCCACAA CAGCCAGGGC AAGGGCAAGG GCAACAAGGG    660
TACTACCCAG GCGCAACTTC CCTGCTGCAG CCAGGACAAG GGCAACAAGG GCCCTACCAG    720
AGTGCAACTT CTCCACAGCA GCCAGGACAA GGACAGGGAC AACAAGAGAC CTATCCAATT    780
GCAACTTCCC CGCATCAGCC AGGACAATGG CAACAACCAG GACAAGGGCA ACAAGGGTTC    840
```

-continued

```
TACCCAAGTG TAACTTCTCC ACAACAGTCG GGACAAGGGC AACAAGGGTA CCCAAGTACA    900
ACTTCTCCAC AACAATCGGG GCAAGGGCAA CAGCTGGGAC AAGGGCAACA ACCAGGACAA    960
GGGCAACAAG GGTACCCAAG TGCAACTTTT CCACAACAGC CAGGACAATG GCAACAAGGG   1020
TCCTACCCAA GTACAACTTC TCCGCAGCAG TCAGGACAAG GGCAACAAGG GTACAACCCA   1080
AGTGGAACTT CTACGCAGCA GCCGGGACAA GTGCAACAGT TGGGACAAGG GCAACAAGGG   1140
TACTACCCAA TTGCAACTTC TCCGCAGCAG CCAGGACAAG GGCAACAGCT AGGACAAGGG   1200
CAACAACCAG GACATGGGCA ACAGCTAGTG CAAGGGCAAC AACAAGGACA AGGGCAACAA   1260
GGACACTACC CAAGTATGAC TTCTCCGCAC CAAACAGGAC AAGGGCAAAA AGGATACTAC   1320
CCAAGTGCAA TTTCTCCGCA GCAGTCAGGA CAAGGACAAC AAGGATACCA GCCTAGTGGA   1380
GCTTCTTCAC AGGGGTCGGT GCAAGGGGCG TGCCAGCACA GCACATCTTC TCCGCAGCAG   1440
CAAGCACAAG GGTGCCAAGC TTCTTCACCA AAGCAAGGGC TAGGGTCGTT GTACTACCCG   1500
AGTGGAGCTT ATACACAACA GAAACCAGGG CAAGGGTACA ACCCAGGTGG AACTTCTCCG   1560
CTGCACCAGC AAGGGGGAGG GTTCGGCGGC GGGTTAACGA CGGAGCAACC GCAGGGAGGA   1620
AAGCAGCCAT TCCATTGCCA GCAAACCACT GTCTCCCCTC ACCAGGGTCA GCAAACCACT   1680
GTTTCCCCTC ATCAGGGTCA GCAAACCACT GTCTCCCCTC ATCAGGGTCA GCAAACCACT   1740
GTCTCCCCTC ACCAGGGTCA GCAAACCACC GTCTCCCCTC ACCAGGGTCA GCAAACCACC   1800
GTCTCCCCTC ATCAGGGTCA GCAAACCACT GTCTCCCCTC ATCCGGGTCA GCAAACCACC   1860
GTCTCCCCTC ATCAGGGTCA GCAAACCACC GTCTCCCCTC ATCAGGGTCA GCAAACCACC   1920
GTCTCCCCTC ATCAGGGTCA GCAGCCCGGC GAGCAGCCTT GCGGTTTCCC TGGCCAGCAA   1980
ACCACCGTGT CTCTGCACCA TGGTCAGCAG TCCAACGAGT TGTACTACGG CAGCCCATAC   2040
CATGTTAGCG TGGAGCAGCC GTCGGCCAGC CTAAAGGTAG CAAAGGCGCA GCAGCTCGCG   2100
GCGCAGCTGC CGGCAATGTG TCGGCTGGAG GGCGGCGGCG GCCTGTTGGC CAGCCAGTAG   2160
TAGAACTCTG GCAGCTCGCA TGGTGCTTGG GCATGCATGC ACCTTAGCTA TACAATAAAC   2220
GTGACGTGTG CTTGCAGTTT TTCATGTAAC TAGGGTAAAA CCCAACAATA ATGCAAAACG   2280
GAAAGCTTCT CCATCC                                                   2296
```

(2) INFORMATION FOR SEQ ID NO:3:

(i) SEQUENCE CHARACTERISTICS:
(A) LENGTH: 479 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:3:

```
CCAGTTCCAT GCAAGCTACC TTCCACTACT CGACATGCTT AAAAGCTTCG AGTGCCCGCC     60
GATTTGCCAG CAATGGCTAA CAGACACATA TTCTGCCAAA ACCCCAGAAC AATAATCACT    120
TCTCGTAGAT GAAGAGAACA GACCAAGATA CAAACGTCCA CGCTTCAGCA AACAGTACCC    180
CAGAACTAGG ATTAAGCCGA TTACGCGGCT TTAGCAGACC GTCCAAAAAA ACTGTTTTGC    240
AAAGCTCCAA TTCCTCCTTG CTTATCCAAT TTCTTTTGTG TTGGCAAACT GCACTTGTCC    300
AACCGATTTT GTTCTTCCCG TGTTTCTTCT TAGGCTAACT AACACAGCCG TGCACATAGC    360
CATGGTCCGG AATCTTCACC TCGTCCCTAT AAAAGCCCAG CCAATCTCCA CAATCTCATC    420
ATCACCGAGA ACACCGAGAA CCACAAAACT AGAGATCAAT TCATTGACAG TCCACCGAG     479
```

(2) INFORMATION FOR SEQ ID NO:4:

(i) SEQUENCE CHARACTERISTICS:
(A) LENGTH: 434 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:4:

```
CTTCGAGTGC CCGCCGATTT GCCAGCAATG GCTAACAGAC ACATATTCTG CCAAAACCCC     60

AGAACAATAA TCACTTCTCG TAGATGAAGA GAACAGACCA AGATACAAAC GTCCACGCTT    120

CAGCAAACAG TACCCCAGAA CTAGGATTAA GCCGATTACG CGGCTTTAGC AGACCGTCCA    180

AAAAAACTGT TTTGCAAAGC TCCAATTCCT CCTTGCTTAT CCAATTTCTT TTGTGTTGGC    240

AAACTGCACT TGTCCAACCG ATTTTGTTCT TCCCGTGTTT CTTCTTAGGC TAACTAACAC    300

AGCCGTGCAC ATAGCCATGG TCCGGAATCT TCACCTCGTC CCTATAAAAG CCCAGCCAAT    360

CTCCACAATC TCATCATCAC CGAGAACACC GAGAACCACA AAACTAGAGA TCAATTCATT    420

GACAGTCCAC CGAG                                                      434
```

(2) INFORMATION FOR SEQ ID NO:5:

(i) SEQUENCE CHARACTERISTICS:
(A) LENGTH: 479 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:5:

```
CCAGTTCCAT GCAAGCTACC TTCCACTACT CGACATGCTT AAAAGCTTCG AGTGCCCGCC     60

GATTTGCCAG CAATGGCTAA CAGACACATA TTCTGCCAAA ACCCCAGAAC AATAATCACT    120

TCTCGTAGAT GAAGAGAACA GACCAAGATA CAAACGTCCA CGCTTCAGCA AACAGTACCC    180

CAGAACTAGG ATTAAGCCGA TTACGCGGCT TTAGCAGACC GTCCAAAAAA ACTGTTTTGC    240

AAAGCTCCAA TTCCTCCTTG CTTATCCAAT TTCTTTTGTG TTGGCAAACT GCACTTGTCC    300

AACCGATTTT GTTCTTCCCG TGTTTCTTCT TAGGCTAACT AACACAGCCG TGCACATAGC    360

CATGGTCCGG AATCTTCACC TCGTCCCTAT AAAAGCCCAG CCAATCTCCA CAATCTCATC    420

ATCACCGAGA ACACCGAGAA CCACAAAACT AGAGATCAAT TCATTGACAG TCCACCGAG     479
```

(2) INFORMATION FOR SEQ ID NO:6:

(i) SEQUENCE CHARACTERISTICS:
(A) LENGTH: 480 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:6:

```
TGTTCCATGC AGGCTACCTT CCACTACTCG ACATGCTTAG AAGCTTTGAG TGGCCGTAGA     60

TTTGCAAAAG CAATGGCTAA CAGACACATA TTCTGCCAAA CCCCAAGAAG GATAATCACT    120

TTTCTTAGAT AAAAAAGAAC AGACCAATAT ACAAACATCC ACACTTCTGC AAACAATACA    180

TCAGAACTAG GATTACGCCG ATTACGTGGC TTTAGCAGAC TGTCCAAAAA TCTGTTTTGC    240

AAAGCTCCAA TTGCTCCTTG CTTATCCAGC TTCTTTTGTG TTGGCAAACT GCGCTTTTCC    300
```

-continued

```
AACCGATTTT GTTCTTCTCG CGCTTTCTTC TTAGGCTAAA CAAACCTCAC CGTGCACGCA    360

GCCATGGTCC TGAACCTTCA CCTCGTCCCT ATAAAAGCCT AGCCAACCTT CACAATCTTA    420

TCATCACCCA CAACACCGAG CACCACAAAC TAGAGATCAA TTCACTGATA GTCCACCGAG    480


(2) INFORMATION FOR SEQ ID NO:7:

     (i) SEQUENCE CHARACTERISTICS:
          (A) LENGTH: 26 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "SYNTHETIC DNA"

    (xi) SEQUENCE DESCRIPTION: SEQ ID NO:7:

TCTCACGTTC AGCGGTGGTG AGAGCC                                         26


(2) INFORMATION FOR SEQ ID NO:8:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "SYNTHETIC DNA"

    (xi) SEQUENCE DESCRIPTION: SEQ ID NO:8:

GTTCCCATTG ATCTCACGTT CAGCG                                          25
```

GENE EXPRESSION REGULATORY DNA, EXPRESSION CASSETTE, EXPRESSION VECTOR AND TRANSGENIC PLANT

BACKGROUND OF THE INVENTION

1. Field of the Invention

The present invention relates to a gene expression regulatory DNA which regulates gene expression within plant cells, and especially to that derived from the barley D-hordein gene.

2. Description of the Related Art

In seeds of barley (Hordeum vulgare), a variety of proteins specifically expressed in seeds (seed storage proteins) are present in large quantities, 35~55% of which are comprised of hordein soluble in alcohol (Shewry, Barley: Chemistry and Technology, pp. 164: American Association of Cereal Chemists, Inc., 1993).

This hordein is classified into four types, B, C, D, and γ based on the genes, loci on chromosome, amino acid sequences, etc. Among them, cDNAs and genomic DNAs of B, C, and γ were isolated and these structural genes and their expression regulatory DNAs have been elucidated.

On the other hand, although cDNA comprising the entire translational region of D-hordein was isolated (Hirota et al., DDBJ, D82941, 1996) and analyzed for its structure, only a partial translational region of its genomic DNA was identified and the 5'-upstream region was found to be relatively short (Sorensen et al., Mol. Genet., 250, 750–760, 1996).

However, although the DNA base sequence of said 5'-upstream region was actually short, composed of 436 bp, this region was qualitatively confirmed to have a promoter activity based on particle bombardment analysis.

The present inventors have carefully studied the Dhordein gene to find the presence of a gene expression regulatory region upstream from the promoter region regulating the expression of D-hordein.

The present invention aims at providing a gene expression regulatory DNA comprised of a promoter region promoting the expression of D-hordein gene and a regulatory region to regulate the expression promoted by said promotor region. In addition, the present invention aims at providing an expression cassette and vector for expressing a desired gene under the regulation of said expression regulatory DNA by utilizing it.

Furthermore, the present invention aims at providing a transgenic plant, a new cultivar, transferred with said expression cassette or said expression vector.

SUMMARY OF THE INVENTION

As described above, (1) the gene expression regulatory DNA of the present invention comprises a promoter region derived from the barley D-hordein gene enabling the expression of a desired gene, and a regulatory region for regulating the expression of said structural gene based on said promoter region.

Based on the construction described above, by linking a desired structural gene to the promoter region derived from said barley D-hordein gene, the expression of said linked structural gene can be specifically regulated by said regulatory region.

Preferably, said regulatory region consists of an activating region to activate the expression of said structural gene based on said promoter region and a suppressing region to suppress the expression of said structural gene based on said promoter region.

That is, the activating region specifically enhances the expression of structural gene linked to said promoter region while the suppressing region specifically reduces it.

This specificity is controlled by tissues and growth stages of plant, and the activating or suppressing region enhances or reduces the expression of structural gene linked to said promoter region according to appropriate tissues or growth stages.

For example, from the abundant expression of said gene for barley D-hordein in seeds, it is inferred that said activating region of said expression regulatory DNA functions in seeds to enhance specifically the expression of structural gene linked to said promoter region, and also that, when seeds advance to the next developing stage, the expression of structural gene linked to said promoter region can be reduced by said suppressing region. Therefore, the construction of regulatory region from that of the barley D-hordein gene will be effective when the specific expression of said structural gene in seeds is attempted.

In addition, the gene expression regulatory region is not necessarily composed of both activating and suppressing regions as described above, and may be constructed only with said activating region according to the specific purpose. In this case, since the expression level of structural gene linked to said promoter region is always kept elevated, such construction provides an effective productive means when the recovery of product of said structural gene is desired.

Said expression regulatory DNA can be obtained from the upstream sequence of the gene for D-hordein on barley chromosome.

More specifically, said expression regulatory DNA is preferably composed of the base sequence described in SEQ ID NO: 1 of the sequence listing or may be composed of a portion thereof having both promoter and expression regulatory activities. Furthermore, said expression regulatory DNA may be composed of base sequences derived from SEQ ID NO:1 with some bases deleted, inserted or substituted, so far as the resulting sequences effectively retain said promoter and expression regulatory activities.

Of said expression regulatory DNA, the promoter region is preferably composed of the base sequence from positions 1,303 to 1,739 of SEQ ID NO: 1 in the sequence listing, and more preferably that from positions 1,446 to 1,739. In addition, these sequences having some bases deleted, inserted or substituted are essentially the same in function as said base sequences, so far as they effectively retain said promoter activity.

On the other hand, said activating region may be composed of the base sequence at least from positions 1,096 to 1,302 in SEQ ID NO:1, or a portion thereof having expression activating capability. Accordingly, it may be composed of the base sequence having the expression activating capability from positions 1,096 to 1,302 of SEQ ID NO:1 and its flanking regions.

More specifically, the base sequence from positions 1,303 to 1,739 derived by the deletion of base sequence from positions 1 to 1302 in SEQ ID NO:1 could not enhance the expression of structural gene linked thereto. On the other hand, the base sequence from positions 1,104 to 1,739 derived by adding a sequence from positions 1,096 to 1,302 to said sequence from positions 1,303 to 1,096 could elevate the expression of structural gene.

Therefore, the activating region may be composed of the entire base sequence from positions 1,096 to 1,302 of SEQ ID NO: 1 or a segment thereof. Alternatively, it is assumed that a part of said activating region may be present downstream from the base at position 1,303 in SEQ ID NO:1, and linked to the base sequence from positions 1,096 to 1,302 or a continuous segment thereof followed by remaining components, eventually producing the complete activating region.

Accordingly, said activating region can be constructed from a base sequence comprising at least a portion of that from positions 1,096 to 1,302 having the expression activating capability. In addition, it may be formed from a sequence having the expression activating capability effectively, even though said sequence is not exactly the same to the sequence described above. That is, even base sequences resulted from partial deletion, insertion or substitution of said base sequence are essentially the same in function to that of the present invention, so far as they possess the expression activating capability.

Also, said expression suppressing region may be constructed from a portion of base sequence of positions 1 to 1,095 of SEQ ID NO:1 possessing the expression suppressing capability.

More specifically, by further linking the base sequence from positions 1 to 1,095 in SEQ ID NO:1 to that comprising said promoter and expression activating regions (specifically, the sequence from positions 1,096 to 1,739 in SEQ ID NO:1), the expression level was reduced to that when only the promoter region was present in the sequence, indicating that said suppressing region possesses the activity to nullify the elevation of expression due to the expression activating region.

Furthermore, the sequence from positions 1 to 1,095 in said SEQ ID NO:1 is sufficient as the expression suppressing region. For example, a portion of this sequence retaining the expression suppressing capability may be used in place of the entire expression suppressing region, and sequences essentially the same in function to said base sequence may be used to substitute said sequence, so far as they possess said expression suppressing effect.

Base sequences of each region described above may be preferably obtained from not only barley DNAs, but also from plants other than barley by hybridization techniques, etc. based on the base sequences herein disclosed. These sequences can be artificially synthesized. A portion of base sequence herein obtained may be used after modified by base substitution, etc.

(2) Said expression regulatory DNA is preferably used as an expression cassette formed by linking to a desired structural gene.

The expression cassette thus formed can be used for the purpose of generating transgenic plants by introducing it directly into a desired plant to integrate it to chromosome, etc.

Alternatively, the expression cassette can be integrated into a desired vector to be used as an expression vector. Expression vectors thus formed can be introduced into plants for the purpose of generating transgenic plants, and also used in the expression system in vitro, etc.

In transgenic plants thus formed, the expression of said structural gene is regulated by the expression regulatory DNA. Although any plants wherein said expression regulatory DNA is capable of functioning properly may be used for the gene transfer, among them barley is preferred.

As plant cells to which said expression cassette or vector is introduced is preferred the maturing seed endosperm tissue wherein the expression of structural gene, which is a foreign gene, is specifically elevated. In addition to this, regeneratable plant cells such as those derived from anther, immature embryo, etc. may be used. Transduction of said expression cassette or vector into plant cells with regeneration potency may provide effective means for ameliorating seeds of barley and other plants, or producing gene products in seeds.

BRIEF DESCRIPTION OF THE DRAWINGS

FIG. 1 represents homology between a portion of the expression regulatory DNA of the present invention (SEQ ID NO:3) and the reported 5'-upstream region of D-hordein gene (SEQ ID NO:4). Asterisks (*) indicate homologous bases in said DNA and gene.

FIG. 2 represents results comparing base sequence of a portion of the expression regulatory DNA of the present invention (SEQ ID NO:5) and that of the promotor region of gene for barley high molecular weight glutenin (SEQ ID NO:6).

FIG. 3 represents results comparing restriction maps of the expression regulatory DNA of the present invention, the promotor region of gene for high molecular weight glutenin, and the known 5' upstream region of reported D-hordein gene.

FIG. 4 is a diagrammatic representation of a process for preparing the expression vector (reporter plasmid) of the present invention.

FIG. 5 is a graphic representation of GUS activity of various expression vectors (reporter plasmids) of the present invention.

FIG. 6 is a graphic representation of GUS activity with the various expression vectors (reporter plasmids) produced by the step-wise deletion of expression regulatory DNA of the present invention.

DESCRIPTION OF THE PREFERRED EMBODIMENT

In the following, preferred embodiments of the present invention will be described.

1. Isolation of Expression Regulatory DNA

Expression regulatory DNA can be isolated from the 5'-upstream region of D-hordein gene on the barley chromosomal DNA. This isolation method comprises three main processes including 1) the one for preparing barley chromosomal DNA, 2) for cloning DNA and 3) for base sequencing.

1) Preparation of Barley Chromosomal DNA

Barley chromosomal DNA can be prepared by standard methods, for example, according to those described in "Cloning and Sequencing—Plant Biotechnology—A Laboratory Manual (Noson Bunkasha), p. 252 (1989)", etc.

2) Isolation of Expression Regulatory DNA and its Cloning

Expression regulatory DNA can be isolated from the 5'-upstream region of the known D-hordein gene with the promoter activity identified (hereafter designated "known region") using standard methods, for example, those described in "Gene Technology Products Guidebook 1995–1996 (Takarashuzo), F-16 (1995)", etc.

In addition to methods described above, said DNA can be isolated by screening chromosomal library prepared by conventional methods with probes homologous to the D-hordein gene, for example, according to those described in "Cloning and Sequencing—Plant Biotechnology—A Laboratory Manual, Noson Bunkasha, p. 134 (1989)", etc.

Also, procedures related to gene cloning necessary for conducting the present invention including the digestion with restriction enzymes, DNA linking procedure, *E. coli* transformation, etc. are performed by standard techniques [ref. Molecular Cloning Manual, Cold Spring Harbor Laboratory (1982)].

3) Determination of Base Sequence

Base sequence of the expression regulatory DNA isolated described above can be determined by the chemical modification method according to Maxam-Gilbert [Methods in Enzymology, 65, 499 (1980)], the dideoxynucleotide chain termination method [Gene, 19, 269 (1982)], etc.

In addition to the method for isolating the expression regulatory DNA from barley described above, said expression regulatory DNA or DNA substantially identical to that can be recovered from other plants using Southern hybridization method based on the base sequence determined as described above. Alternatively, said expression regulatory DNA can be artificially synthesized using a DNA synthesizer based on said base sequence.

2. Construction of Expression Cassette and Vector, and its Expression in Cells

1) Preparation of Expression Cassette

Expression cassette can be prepared by linking a desired structural gene downstream from said expression regulatory DNA followed by linking transcription terminating factor such as NOS terminator downstream from said structural gene. Expression cassette thus prepared may be transferred directly as such in a linear form into plant chromosomes or integrated into a desired plasmid to be used as expression vector described below.

2) Preparation of Expression Vector

As described above, expression vector can be prepared by integrating said expression cassette into a desired plasmid. Alternatively, it may be prepared by linking successively expression regulatory DNA, structural gene and transcription factor to said plasmid. Any plasmid such as commercially available plasmid pBI101 (Clontec) may be used, but preferably selected according to the purpose of its use.

For example, it is preferable to select plasmid with the replication origin suitable to organisms to which said expression vector is transferred. Also, when the replication is intended in both different organisms (e.g., *E. coli* and plant such as barley), it is preferred to use shuttle vector comprising the replication origins of both. When expression vector is recovered in large quantities, it is preferable to select plasmid with large copy numbers.

Furthermore, as the plasmid described above, the one provided with selection markers based on drugs or nutrients can be selected for the detection of said expression vector transferred into organisms.

Expression vector or cassette as described above can be prepared by standard techniques [e.g., Molecular Cloning Manual Cold Spring Harbor Laboratory (1982)].

3) Transfer of Expression Cassette or Vector into Plants

Cells to which said expression cassette or vector is introduced comprise plant cells such as maturing seed endosperm cells and those with regeneration potency including cells derived from anther and immature embryo.

Expression cassette or vector can be transferred into plant cells by standard methods [Plant Cell Reports, 10, 595 (1992)], including, in addition to polyethylene glycol method, electroporation method [e.g., ref. Nature, 319, 791 (1986)], particle gun method [e.g., ref. Nature, 327, 70 (1987)], laser poration method [e.g., ref. Barley Genetics VI, 231 (1991) and Agrobacterium-mediated method [e.g., Plant J., 6, 271 (1994)].

For example, said expression cassette or said expression vector can be transferred into maturing seed endosperm of barley by standard methods such as polyethylene glycol method after protoplasts are prepared from said endosperm.

4) Transgenic Plants

As described above, transgenic plants can be created by transferring a foreign DNA integrated into expression cassette or vector into plants, forming a novel cultivar with different properties from those of wild type plant.

For example, when the structural gene comprised in expression cassette or vector is the one related to the plant generation and growth, the harvest time or yield can be controlled through germination and growth of transgenic plants. When said structural gene is the one related to plant components, it is possible to obtain a novel cultivar of plant.

EXAMPLES

The present invention is further illustrated by the following examples, which should not be construed as limiting in any way.

Example 1

Preparation of Barley Chromosomal DNA and its Digestion with Restriction Enzyme

After green leaves of barley (Haruna Nijo) cultivated in a test farm were lyophilized, chromosomal DNA was extracted from the freeze-dried tissues. Total DNA thus obtained (5 μg) was completely digested with restriction enzyme PstI (50 units). The DNA fraction was precipitated with ethanol, and then dissolved in sterilized water (10 μl).

Example 2

Linking of Adaptor DNA

PstI-digested barley (Haruna Nijo) DNA (2.5 μg) was ligated to a PstI adaptor (Takarashuzo, 5 μl) using a ligation kit (Takarashuzo) by incubating at 16° C. for 30 min. The adaptor-ligated DNA was precipitated with ethanol, dissolved in sterilized water (5 μl), and used as a template DNA for PCR.

Example 3

Synthesis of Primers Specific for D-hordein Gene

Based on the sequence of SEQ ID NO:2, a set of primer DNAs comprising the following sequence of the 5'-terminus nearing region of D-hordein gene was synthesized:

5'-TCTCACGTTCAG-CGGTGGTGAGAGCC-3' (primer DHP1) (SEQ ID NO: 7) and

5'-GTTCCCATTGATCTCACGTTCAGCG-3' (primer DHP2) (SEQ ID NO:8).

Example 4

Amplification of 5'-upstream Region of D-hordein Gene by PCR

For the first amplification, the reaction solution comprised the template DNA obtained in Example 2 (1.0 μl), primer DHP2 (100 μM, 1.0 μM), primer C1 (Takarashuzo) (100 μM, 1.0 μl), dNTP mix (2.5 mM each, 4.0 μl) and a magnesium-containing 10×PCR buffer (Boehringer) (5.0 1), a thermostable DNA polymerase (Expand High Fidelity, Boehringer) (0.5 μl), and further sterilized water (37.5 μl). The reaction was performed using a thermal controller (MJ Research) with 30 temperature cycles wherein, after the initial duplex denaturation at 94° C. for 2 min, each cycle comprised annealing at 60° C. for 30 s, DNA synthesis at 68° C. for 3 min, and denaturation at 94° C. for 15 s. On agarose gel electrophoresis, the PCR amplification products thus obtained showed no specifically amplified DNA bands.

The second amplification was performed using a similar reaction solution described above which was modified by comprising the first PCR amplification products as a template DNA (1.0 μl), primer DHP1 (100 μM, 1.0 μl) and primer C2 (Takarashuzo) (100 μM, 1.0 μl) under similar conditions as in the first amplification. Agarose electrophoresis of the PCR amplification products thus obtained revealed a specifically amplified band at around 1.8 kb.

Example 5

Cloning of PCR Amplification Products

After the agarose gel electrophoresis of said PCR amplification products, 1.8 kb band was excised from the gel, purified by glass-milk method (Bio101), and end-blunted using a blunting kit (Takarashuzo). This segment was cloned into the HincII site of cloning vector pUC118 to obtain a DPP3 clone.

Example 6

Structural Analysis of DPP3 Clone

Structural analysis of DPP3 clone was performed by the successive deletion from both termini of DNA. Deletion mutants were prepared by cleaving DNA at about 200 bp intervals from both termini according to the instruction provided with a deletion kit (Takarashuzo), and structurally analyzed by the dideoxy nucleotide chain termination method.

SEQ ID NO:1 in the sequence listing shows the structure determined of 5'-upstream region (DPP3) of D-hordein gene, designated the expression regulatory DNA hereafter.

Since the expression regulatory DNA thus obtained comprises the sequence homologous to that of the 5'-terminus region of D-hordein cDNA shown in SEQ ID NO:2 of the sequence listing, DNA segments thus obtained were assumed to contain at least the promoter region of D-hordein. More specifically, SEQ ID NO:2 comprises the structural D-hordein gene region. In addition, a portion of the promoter region upstream from the translational initiation codon ATG (corresponding to positions 37~39) in SEQ ID NO:2 was identical to that of the promoter region of the expression regulatory DNA in SEQ ID NO:1 (from positions 1704~1739).

Also, in the promoter region of said expression regulatory DNA was identified the GCN4 box (GAGTCA) (positions from 1153 to 1158 and from 1174 to 1179 in SEQ ID NO:1 of the sequence listing) which is often found in the promoter for many seed storage proteins and required for effective expression in maturing seeds, in addition to the TATA box widely present in the promoter region of eukaryotes.

FIG. 1 shows the homology between a partial base sequence of the expression regulatory DNA as obtained above (upper row) (SEQ ID NO:4) and the 5'-upstream region of the reported D-hordein gene (designated the known region hereafter) (lower row).

The base sequence of the expression regulatory DNA obtained above was compared with that of the reported promoter region. FIG. 2 shows a base sequence portion of the expression regulatory DNA obtained above compared with that of the promoter region of high molecular weight glutenin gene of wheat, wherein the upper row represents a portion of the expression regulatory DNA (base Nos. from 1261 to 1739) (SEQ ID NO:5), and the lower row the promoter region of said reported high molecular weight glutenin (SEQ ID NO:6).

FIG. 3 represents comparison results of restriction maps of the expression regulatory DNA (A), known region (B) and promoter region of high molecular weight glutenin gene (C).

Example 7

Reporter Plasmid (Preparation of Expression Vector)

FIG. 4 is a schematic representation of each process for reporter plasmid preparation. A HindIII-EcoRI segment of plasmid pBI101 (Clontech) containing GUS gene and NOS terminator was inserted to HindIII and EcoRI sites of plasmid pUC118 to form pBI11 serving as the negative control vector (FIG. 4A). As the positive control vector was used pACT1F structurally expressed in rice plant and barley (not shown).

On the other hand, a reporter plasmid containing the desired expression regulatory DNA (DPP3) was linked with GUS gene and NOS terminator downstream from DPP3. More specifically, plasmid DPP3HD prepared by deleting the HindIII segment from DPP3 was digested with Bpu1102I, end-blunted, and further digested with EcoRI. To this EcoRI site was inserted a SmaI-EcoRI segment containing GUS gene and NOS terminator of pBI101 to form a plasmid DPP3HDGUS9. Then, to the HindIII site of DPP3HDGUS9 was re-inserted the HindIII segment deleted previously to form the reporter plasmid (DPP3GUS2) (FIG. 4B).

Example 8

Deletion of Promoter Region from Reporter Plasmid DPP3GS2

Using a deletion kit, base segments were deleted successively from the 5'-terminus of the reporter plasmid DPP3GUS2 obtained in Example 7 to construct various reporter plasmids. More specifically, they comprise the following bases of SEQ ID NO:1: reporter plasmid DPP3GUS2Δ32 from positions 219 to 1739, DPP3GUS2Δ16 from positions 1096 to 1739, DPP3GUS2Δ42 from positions 1198 to 1739, DPP3HDGUS9 from positions 1303 to 1739, DPP3GUS2Δ47 from positions 1446 to 1739, and DPP3GUS2Δ22 from positions from 1526 to 1739.

Example 9

Detection of Promoter Activity in Maturing Seed Endosperm

Activity of the promoter region of D-hordein gene isolated from maturing seed endosperm was determined by a transient assay system using reporter plasmid described in Example 7

Maturing seeds of barley (cultivar Bomi), around 14 days after flowering, were first husked, sterilized with 70% ethanol and a 5-fold diluted hypochlorite solution once each, and then washed with water three times. Endosperm was thrusted out, and treated with a CPW solution (consisting of 0.2 mM $KH_2PO_4$, 10 mM $CaCl_2$, 1 mM $MgSO_4$ and 1 mM $KNO_3$) containing 4% cellulase and 11% mannitol at 25° C. overnight.

After protoplasts thus obtained were washed with a CPW solution containing 11% mannitol, they were dispensed to tubes at $10^6$ protoplasts per one transformation system, suspended by adding DNA (30 μg) and a C100S solution [consisting of 7% sorbitol, 100 mM $CaCl_2$and 4.7 mM MES (pH 5.7)] (200 μl). To this suspension was added a C100S solution (pH 7.0) containing 40% polyethylene glycol, and the mixture was incubated for 10 min. To the above mixture was added an LW solution [Theor. Appl. Genet., 81: 437 (1991)] (10 ml), and the resulting mixture was centrifuged. To the precipitates was added an L1 solution [Theor. Appl. Genet., 81: 437 (1991)] (3 ml), and the mixture was incubated at 25° C. overnight. To this incubation mixture was added an LW solution (20 ml), and the mixture was centrifuged. Precipitates thus obtained were suspended in a GUS extraction solution (consisting of 0.05 M $Na_3PO_4$, 0.01 M EDTA, 0.1% sarkosyl, 0.1% TritonX-100 and 0.1% 2-mercaptoethanol) (200 μl), Freeze-thawed twice, centrifuged, and the supernatant was used as crude enzyme solution for the promoter activity assay. That is, after the crude enzyme solution thus obtained was reacted with 4-methylumbelliferyl-β-D-glucuronide, the reaction was terminated with 0.2 M sodium carbonate, and the amount of 4-methylumbelliferone produced was assayed to express the promoter activity. Quantitation of proteins was carried out using a "Protein Assay" (BioRad).

GUS activity expressed in barley protoplasts transferred with various expression vectors is shown in FIG. 5. The figure shows that protoplasts of maturing barley seed transferred with the reporter plasmid DPP3GUS2 comprising the isolated D-hordein promoter region expressed about 1.5 times higher GUS activity as compared with those transferred with pACT1F vector, indicating that said expression regulatory DNA had the promoter activity.

Example 10

Detection of Deletion Promoter Activity in Maturing Seed Protoplasts

In a similar manner as described in Example 9, each deletion reporter plasmid obtained in Example 8 was transferred to maturing barley seed protoplasts, and then GUS activity was assayed. GUS activity in protoplasts transferred with each deletion vector is shown in FIG. 6. This figure clearly indicates that little GUS activity was expressed with plasmid DPP3GUS2Δ22 comprising a short promoter region, while the enzyme activity was increased with the increasing length of promoters from DPP3GUS2Δ47 to DPP3HDGUS9. After GUS activity was once decreased with DPP3GUS2Δ42, it reached highest with DPP3GUS2Δ16. However, with DPP3GUS2Δ32 and DPP3GUS2 comprising the full-length promoter, the enzyme activity was suppressed again.

In plants, promoter is generally regulated in vivo for the expression level of gene by plant conditions including tissue involved, developing stage, nutritional status, etc. That is, promoter is provided with a regulatory region not only to increase but also suppress the gene expression level, conducting a balanced gene expression in plants. In this regard, analyses of GUS activity and D-hordein promoter activity in seed protoplasts 14 days post-flowering indicated that a region promoting the expression of D-hordein gene (activating region) is located between bases from positions 1303 to 1739 (DPP3HDGUS9) in SEQ ID NO: 1, and a region regulating suppressively the expression of D-hordein gene is present between bases from positions 1 to 1095 (suppressing region). These results indicate that the co-operation of these respective regions in vivo would enable the balanced effective expression of D-hordein.

The present invention elucidated base sequence of the expression regulatory DNA and the effective transcriptional regulation in maturing barley seeds. Expression cassette wherein this expression regulatory DNA is linked to an appropriate foreign structural gene and a transcription terminating factor, or expression vector wherein said cassette is integrated into plasmid may be introduced into barley or other plants. By transferring the expression regulatory DNA into plants, transgenic plants having seeds of barley or other plants intentionally improved, or those useful as the tool for producing gene products in seeds can be generated.

Accordingly, said expression regulatory DNA may contribute to plant breeding or plant rearing and cultivating through the breeding.

We claim:

1. A DNA for regulating the expression a structural gene, comprising:

(1) a promoter region derived from the barley D-hordein gene, and (2) at least one regulatory sequence selected from the group consisting of (a) an activating region comprising at least the base sequence from positions 1,096 to 1,302 of SEQ ID NO: 1, and (b) a suppressing region comprising at least the base sequence from positions 1 to 1,095 of SEQ ID NO: 1, wherein (1) and (2) are operably linked such that when further operably linked to the structural gene the DNA regulates the expression of the structural gene.

2. The DNA of claim 1, wherein (2) contains (a).

3. The DNA of claim 1, wherein (a) consists of positions 1,096 to 1,302 of SEQ ID NO: 1.

4. The DNA of claim 1, wherein (2) contains (b).

5. The DNA of claim 1, wherein (b) consists of positions 1 to 1,095 of SEQ ID NO: 1.

6. The DNA of claim 1, wherein (2) contains (a) and (b).

7. The DNA of claim 6, wherein (a) consists of positions 1,096 to 1,302 of SEQ ID NO: 1 and (b) consists of positions 1 to 1,095 of SEQ ID NO: 1.

8. The DNA of claim 1, wherein (1) comprises positions 1,303 to 1,739 of SEQ ID NO: 1.

9. The DNA of claim 8, wherein (2) contains (a).

10. The DNA of claim 9, wherein (a) consists of positions 1,096 to 1,302 of SEQ ID NO: 1.

11. The DNA of claim 8, wherein (2) contains (b).

12. The DNA of claim 11, wherein (b) consists of positions 1 to 1,095 of SEQ ID NO: 1.

13. The DNA of claim 8, wherein (2) contains (a) and (b).

14. The DNA of claim 13, wherein (a) consists of positions 1,096 to 1,302 of SEQ ID NO: 1 and (b) consists of positions 1 to 1,095 of SEQ ID NO: 1.

15. The DNA of claim 1, wherein the DNA consists of positions 1 to 1,739 of SEQ ID NO: 1.

16. A gene expression cassette, comprising the DNA of claim 1, operably linked to a structural gene.

17. An expression vector comprising the gene expression cassette of claim 16.

* * * * *

UNITED STATES PATENT AND TRADEMARK OFFICE

CERTIFICATE OF CORRECTION

PATENT NO. : 5,955,649
DATED : September 21, 1999
INVENTOR(S) : Naohiko Hirota et al.

It is certified that error appears in the above-identified patent and that said Letters Patent is hereby corrected as shown below:

Title page,
"17 Claims, No Drawings" should read -- 17 Claims, 6 Drawing Sheets --.

Signed and Sealed this

Sixth Day of August, 2002

*Attest:*

JAMES E. ROGAN

*Attesting Officer* *Director of the United States Patent and Trademark Office*